(12) United States Patent
Laver

(10) Patent No.: US 6,197,861 B1
(45) Date of Patent: Mar. 6, 2001

(54) STABILIZATION OF PAINTS WITH SPIROINDANE DERIVATIVES

(75) Inventor: Hugh Stephen Laver, Reinach (CH)

(73) Assignee: Vantico Inc., Brewster, NY (US)

( * ) Notice: Subject to any disclaimer, the term of this patent is extended or adjusted under 35 U.S.C. 154(b) by 0 days.

(21) Appl. No.: 09/230,395

(22) PCT Filed: Jun. 21, 1997

(86) PCT No.: PCT/EP97/03271

§ 371 Date: Jan. 27, 1999

§ 102(e) Date: Jan. 27, 1999

(87) PCT Pub. No.: WO98/01507

PCT Pub. Date: Jan. 15, 1998

(30) Foreign Application Priority Data

Jul. 3, 1996 (EP) ................................................ 96810440

(51) Int. Cl.⁷ .................................................... C08K 5/06
(52) U.S. Cl. .......................................................... 524/367
(58) Field of Search ............................................ 524/367

(56) References Cited

U.S. PATENT DOCUMENTS

| 4,416,978 | 11/1983 | Morigaki et al. | 430/548 |
| 5,411,847 | * 5/1995 | Leppard et al. | 430/551 |

FOREIGN PATENT DOCUMENTS

| 0355660 | 2/1990 | (EP) . |
| 0636669 | 2/1995 | (EP) . |
| 2062888 | 5/1981 | (GB) . |
| 2077455 | 12/1981 | (GB) . |
| 2201254 | 8/1988 | (GB) . |

* cited by examiner

*Primary Examiner*—Edward J. Cain
(74) *Attorney, Agent, or Firm*—Luther A. R. Hall; Michele A. Kovaleski

(57) ABSTRACT

Paint or coating compositions are stabilized by spiroindane compounds of the following formula

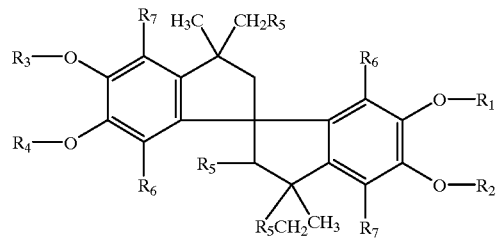

wherein the numbered radicals R have he meanings given in claim 1,
and optionally phosphite stabilizers and phenolic antioxidants.

9 Claims, No Drawings

STABILIZATION OF PAINTS WITH SPIROINDANE DERIVATIVES

The invention relates to coating compositions containing spiroindane compounds and to novel spiroindane compounds.

Antioxidants are needed in thermosetting coatings to prevent oxidation of the binder on curing and overbaking. $NO_x$ present in the burner gases of ovens causes an additional problem by reacting, with preferentially aromatic components in the binder, to form yellow breakdown products.

It is the usual practice in paints to use a stabiliser combination of a hindered phenol and a phosphite, for example octadecyl-3-(3,5-di-tert-butyl-4-hydroxyphenyl) propionate or tetrakis-(3-(3,5-di-tert-butyl-4-hydroxyphenyl)-propionyloxymethyl)methane with 2,4-di-tert-butylphenylphosphite.

For better gas oven stability a phosphite is usually used alone.

DE-A-4306 747 teaches the use of the combination of a phosphite and a 2,2,6,6-tetramethylpiperidine compound (HALS) in one molecule as stabiliser for powder paints.

Phosphites on their own give only slight protection against oxidation in air. In the presence of $NO_x$ they mostly do not yellow, but remain largely ineffective.

The hindered phenols give much better protection against oxidation, particularly when used together with phosphites, but are themselves highly prone to yellowing in the presence of $NO_x$.

A number of patents by Fuji Photo Film KK claim the spiroindanes and their use in colour photographic films and papers as light fading preventing agents for the magenta pyrazolone-azomethine and pyrazolotriazole-azomethine dyes: GB-A-2077 455, DE-A-3221 883, JP-A-57204 035 and EP-A-355 660. U.S. Pat. No. 5,411,847 and GB-A-2 201 254 disclose similar structures in photographic applications.

The present invention is based on the discovery that the problem of yellowing of paints on curing in gas(or oil-)-fired ovens can be solved through use of certain specific spiroindane derivatives, either alone or with other stabilisers, preferably phosphites.

The invention relates to a composition comprising:
(A) a powder coating material
(B) at least one compound of formula

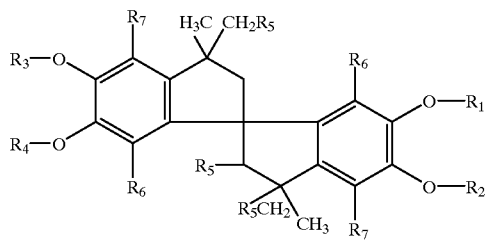

(I)

wherein $R_1, R_2, R_3$ and $R_4$ are independently of one another:
a) $C_1$–$C_{18}$ unsubstituted alkyl or $C_1$–$C_{18}$alkyl substituted by one or more of the groups OH, $C_1$–$C_{18}$alkoxy, $C_2$–$C_{18}$alkenyloxy, halogen, phenoxy (which is unsubstituted or substituted by $C_1$–$C_{18}$alkyl, $C_1$–$C_{18}$alkoxy or halogen), $COOR_8$, —$CONH_2$, —$CONHF_9$ or —$CONR_9R_{10}$;

b) $C_5$–$C_{12}$cycloalkyl which is unsubstituted or substituted by OH or —$OCOR_{11}$;
c) a five or six-membered heterocycle that is saturated or unsaturated;
d) $C_7$–$C_{11}$ phenylalkyl, which is unsubstituted or substituted by one or more OH, Cl or $CH_3$;
e) $C_2$–$C_{18}$alkenyl;
f) $C_4$–$C_{30}$ alkyl which is interrupted by one or more O atoms and can be substituted by OH;
g) —CO—$R_{12}$ or —$(CH_2)_n$—CO—$R_{12}$;
h) —$SO_2$—$R_{13}$;

i) a group

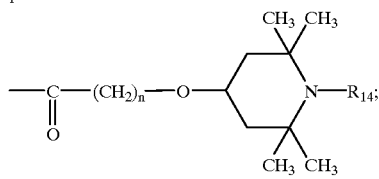

j) a group

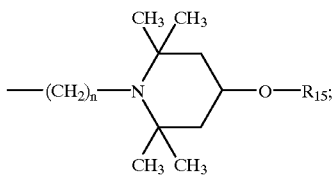

k) a group

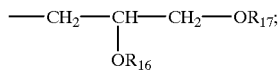

n is 1 to 18;

$R_5$ is H, $C_1$–$C_{18}$ straight chain or branched alkyl, $C_2$–$C_{18}$alkenyl or $C_6$–$C_{12}$aryl;

$R_6$ and $R_7$ are independently of one another H, halogen, $C_1$–$C_{18}$alkyl, $C_2$–$C_6$alkenyl, $C_1$–$C_{12}$alkoxy or $C_2$–$C_{12}$alkenyloxy;

$R_8$ is $C_1$–$C_{18}$alkyl, $C_2$–$C_{18}$alkenyl, $C_3$–$C_{20}$ alkyl which is interrupted by one or more O, $NR_9$ or S and/or substituted by OH, $C_1$–$C_4$alkyl which is substituted by —$P(O)(OR_{18})_2$, $C_3$–$C_8$alkynyl or $C_7$–$C_{11}$ phenylalkyl;

$R_9$ and $R_{10}$ are independently of one another $C_1$–$C_{12}$alkyl, $C_3$–$C_{12}$alkoxyalkyl, $C_4$–$C_{16}$dialkylaminoalkyl or $C_5$–$C_{12}$cycloalkyl, or $R_9$ and $R_{10}$ together are $C_3$–$C_9$alkylene or $C_3$–$C_9$oxaalkylene or $C_3$–$C_9$azaalkylene;

$R_{11}$ is $C_1$–$C_{18}$alkyl, $C_2$–$C_{18}$alkenyl or phenyl;

$R_{12}$ is $C_1$–$C_{18}$alkyl, $C_2$–$C_{18}$alkenyl, phenyl, $C_1$–$C_{12}$alkoxy, phenoxy, $C_1$–$C_{12}$alkylamino or $C_6$–$C_{12}$arylamino or a group —$R_{19}$—COOH;

$R_{13}$ is $C_1$–$C_{12}$alkyl, $C_6$–$C_{12}$aryl or $C_7$–$C_{14}$alkaryl;

$R_{14}$ is hydrogen, oxyl, hydroxy, —$CH_2CN$, $C_1$–$C_{18}$alkyl, $C_1$–$C_{18}$— alkoxy, $C_3$–$C_8$alkenyl, $C_3$–$C_8$alkynyl, $C_5$–$C_8$cycloalkyl or -alkoxy, phenyl, naphthyl, $C_7$–$C_{12}$phenylalkyl or -alkoxy, phenyl or phenylalkyl substituted by alkyl or phenyl of 7–14 carbon atoms, $C_3$–$C_5$alkenoyl, $C_1$–$C_{18}$ alkynoyloxy, benzyloxy or a group $CH_2$—CH(OH)—Z where z is H, $CH_3$ or Phenyl, or a group of the formula

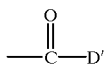

wherein

D' is $C_1$–$C_{18}$alkyl, $C_1$–$C_{18}$alkoxy, phenyl, or phenyl substituted by hydroxy, $C_1$–$C_8$alkyl, $C_1$–$C_8$alkoxy, amino or amino mono- or disubstituted by $C_1$–$C_8$alkyl or phenyl.

$R_{15}$ is H, $C_1$–$C_{18}$alkyl or $C_3$–$C_{18}$alkyl interrupted by one or more oxygen atoms, cyanoethyl, benzyl, glycidyl, a monovalent radical of an aliphatic, cycloaliphatic, araliphatic or aromatic carboxylic acid, or of carbamic acid, or of a phosphorus-containing acid, or a monovalent silyl radical —Si($R_{21}$)($R_{22}$)($R_{23}$);

$R_{16}$ is H, —CO—$R_{11}$, —Si($R_{21}$)($R_{22}$)($R_{23}$), or —COO$R_{24}$;

$R_{17}$ is $C_1$–$C_{18}$ alkyl, $C_2$–$C_{18}$ alkenyl, phenyl-$C_1$–$C_4$alkyl, $C_3$–$C_{24}$alkyl or $C_2$–$C_{14}$hydroxyalkyl, each of which is interrupted by one or more O atoms, or is phenyl, which is unsubstituted or substituted by $C_1$–$C_4$alkyl, $C_1$–$C_4$alkoxy or halogen, $C_5$–$C_{12}$cycloalkyl which is unsubstituted or substituted by 1–3 $C_1$–$C_8$ alkyl, or —CO$R_{11}$, or

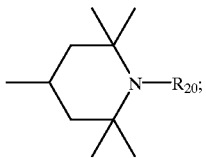

$R_{18}$ is $C_1$–$C_{18}$alkyl or phenyl;

$R_{19}$ is $C_1$–$C_{18}$alkylene, vinylene or phenylene;

$R_{20}$ is H, OH, oxyl, $C_1$–$C_{18}$alkyl, $C_2$–$C_{18}$alkenyl, $C_1$–$C_{18}$alkoxy, $C_5$–$C_{12}$cycloalkyl, $C_5$–$C_{12}$cycloalkoxy, $C_3$–$C_8$alkynyl, $C_7$–$C_{12}$phenylalkyl, $C_1$–$C_8$alkanoyl, $C_3$–$C_5$alkenoyl or glycidyl;

$R_{21}$, $R_{22}$ and $R_{23}$ are independently of one another $C_1$–$C_6$alkyl or phenyl;

Preferred spiroindane derivatives which can be used according to the invention are of formula I, herein $R_5$ is H;

$R_1$, $R_2$, $R_3$ and $R_4$ are the same and can be a) $C_1$–$C_{18}$ straight chain or branched alkyl, optionally substituted by one or more of the groups OH, $C_1$–$C_{18}$alkoxy, $C_2$–$C_{18}$alkenyloxy, —COO$R_8$, —CONH$_2$, —CONH$R_9$, —CON$R_9R_{10}$;

b) $C_5$–$C_{12}$cycloalkyl which is unsubstituted or substituted by OH or —OCO$R_1$ i c) tetrahydropyran;

e) $C_2$–$C_{18}$alkenyl;

f) $C_4$–$C_{30}$ alkyl which is interrupted by one or more O atoms and can be substituted by OH;

g) —CO—$R_{12}$ or —(CH$_2$)$_n$—CO—$R_{12}$;

i) a group

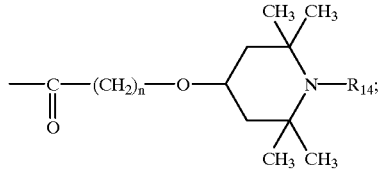

j) a group

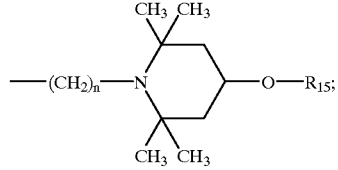

k) a group

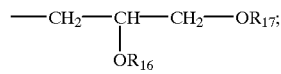

n is 1 to 18;

$R_6$ and $R_7$ are independently of one another H or $C_1$–$C_8$alkyl;

$R_8$ is $C_1$–$C_{18}$alkyl, $C_2$–$C_{18}$alkenyl, $C_3$–$C_{20}$ alkyl which is interrupted by one or more 0 or substituted by OH or is $C_3$–$C_8$alkynyl;

$R_9$ and $R_{10}$ are independently of one another $C_1$–$C_{12}$alkyl, $C_3$–$C_{12}$alkoxyalkyl or $C_5$–$C_{12}$cycloalkyl;

$R_{11}$ is $C_1$–$C_{18}$alkyl or $C_2$–$C_{18}$alkenyl;

$R_{12}$ is $C_1$–$C_{18}$alkyl, $C_2$–$C_{18}$alkenyl, $C_1$–$C_{12}$alkoxy, $C_1$–$C_{12}$alkylamino or a group $R_{19}$—COOH, $R^{14}$ is especially $C_1$–$C_{12}$alkyl, allyl, cyclohexyl, benzyl, acetyl, acryloyl, Cyclohexyloxy or $C_1$–$C_{12}$-alkyoxy $R_{15}$ is H or $C_1$–$C_{18}$alkyl optionally interrupted by one or more oxygen atoms;

$R_{16}$ is H, —CO—$R_{11}$, —Si($R_{21}$)($R_{22}$)($R_{23}$), or —COO$R_{24}$;

$R_{17}$ is $C_1$–$C_{18}$ alkyl, $C_2$–$C_{18}$ alkenyl, $C_3$–$C_{24}$alkyl or $C_2$–$C_{14}$hydroxyalkyl, each of which is interrupted by one or more O atoms, $C_5$–$C_{12}$cycloalkyl which is unsubstituted or substituted by 1–3 $C_1$–$C_8$ alkyl, or —CO$R_{11}$, or is

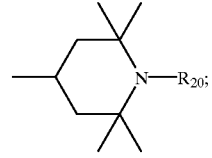

$R_{19}$ is $C_1$–$C_{18}$alkylene or vinylene;

$R_{20}$ is H, OH, oxyl, $C_1$–$C_{18}$alkyl, $C_2$–$C_{18}$alkenyl, $C_1$–$C_{18}$alkoxy, $C_5$–$C_{12}$cycloalkyl, $C_5$–$C_{12}$cycloalkoxy, $C_3$–$C_8$alkynyl, $C_1$–$C_8$alkanoyl, $C_3$–$C_5$alkenoyl or glycidyl;

$R_{21}$, $R_{22}$ and $R_{23}$ are independently of one another $C_1$–$C_6$alkyl;

$R_{24}$ is $C_1$–$C_4$alkyl.

Particularly preferred spiroindane derivatives which can be used according to the invention are of formula I wherein $R_5$, $R_6$ and $R_7$ are H;

$R_1, R_2, R_3$ and $R_4$ are the same and can be either:
a) $C_1$–$C_{18}$ straight chain or branched alkyl;
b) cyclohexyl;
e) allyl;
f) $C_3$–$C_{12}$ alkyl which is interrupted by one or more O atoms;
g) —CO—$R_{12}$;

i) a group

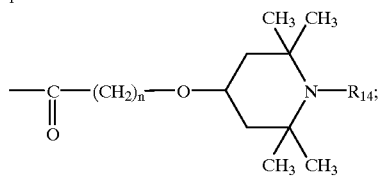

j) a group

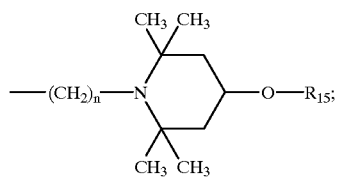

k) a group

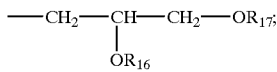

n is 1 to 6;
$R_{12}$ is $C_1$–$C_4$alkyl or $C_2$–$C_3$alkenyl;
$R_{14}$ is $C_1$–$C_{12}$alkyl, benzyl, or $C_5$–$C_8$cycloalkyl; most preferably $C_6$–$C_{10}$alkyl or cyclohexyl.
$R_{15}$ is H or $C_1$–$C_{18}$alkyl optionally interrupted by one or more oxygen atoms;
$R_{16}$ is H, —CO—$R_{11}$ or —COO$R_{24}$;
$R_{17}$ is $C_1$–$C_{18}$ alkyl, $C_2$–$C_{18}$ alkenyl, $C_3$–$C_{24}$alkyl or $C_2$–$C_{14}$hydroxyalkyl, each of which is interrupted by one or more O atoms or is $C_5$–$C_{12}$cycloalkyl; or is

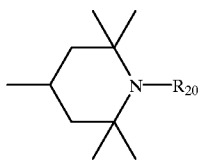

$R_{20}$ is H, $C_1$–$C_8$alkyl, acetyl, propargyl, acryloyl, $C_1$–$C_8$alkoxy or $C_5$–$C_{12}$cycloalkyl;
$R_{24}$ is $C_1$–$C_4$alkyl.

An alkyl radical of 1 to 30 carbon atoms may be straight-chain or branched and be typically: methyl, ethyl, propyl, isopropyl, n-butyl, sec-butyl, isobutyl, tert-butyl, pentyl, isopentyl, hexyl, heptyl, 3-heptyl, octyl, 2-ethylhexyl, nonyl, decyl, undecyl, dodecyl, tridecyl, tetradecyl, pentadecyl, hexadecyl, heptadecyl, octadecyl, eicosyl, henicosyl, docosyl, 2-ethylbutyl, 1-methylpentyl, 1,3-dimethylbutyl, 1,1,3,3-tetramethylbutyl, 1-methylhexyl, isoheptyl, 1-methylheptyl, 1,1,3-trimethylhexyl, 1,1,3,3-tetramethylhexyl or 1-methylundecyl. Preferably $R_1$ is an alkyl radical of 1 to 18carbon atoms.

Examples of alkoxy radicals are derived from the above groups by addition of the group —O—.

Alkenyl radicals are derived from alkyl radicals by the replacement of one or more than one C—C single bond by C=C double bonds. Allyl and isoallyl are preferred. Alkenyloxy is derived from alkenyl by adding —O—. Illustrative examples for alkenyl of 2 to 18 carbon atoms are vinyl, allyl, 2-methallyl, butenyl such as 2-butenyl, hexenyl such as 2-hexenyl, decenyl, undecenyl such as 10-undecenyl, heptadecenyl or oleyl.

$C_5$–$C_{12}$cycloalkyl radicals typically include cyclopentyl, cyclohexyl, cycloheptyl, cyclooctyl, cyclodecyl and cyclododecyl. Cyclopentyl, cyclohexyl and cycloheptyl are preferred and cyclohexyl is particularly preferred. Cycloalkoxy radicals and cycloalkoxycarbonyl radicals are derived from said $C_5$–$C_{12}$cycloalkyl radicals by adding —CO— or —O—CO— groups. Phenyl-$C_{14}$alkyl and $C_7$—$C_9$phenylalkyl are typically benzyl, phenethyl, 3-phenylpropyl, a-methylbenzyl and a,a-dimethylbenzyl. Benzyl is preferred.

Typical examples of the above unsubstituted or $C_1$–$C_8$alkyl-substituted cycloalkyl groups of 5 to 12 carbon atoms are cyclopentyl, cyclohexyl, cyclooctyl, cyclododecyl, 2- or 4-methylcyclohexyl, dimethylcyclohexyl, trimethylcyclohexyl, tert-butylcyclohexyl. Cyclohexyl is especially preferred.

$C_3$–$C_8$alkynyl is derived from the alkyl radicals having 3 to 8 C atoms in which 2 C atoms are connected by a triple bond and is preferably propargyl.

$C_6$–$C_{12}$-aryl refers to e.g. phenyl or naphthyl.
$C_7$–$C_{18}$phenylalkyl can be typically benzyl, 1- or 2-phenylethyl, 3-phenylpropyl, a,a-dimethylbenzyl, 2-phenylisopropyl, 2-phenylhexyl or benzhydryl. Benzyl is preferred.

$C_7$–$C_{18}$alkylphenyl may contain linear or branched alkyl groups, the number of said alkyl groups being 1 to 3, preferably 1 or 2. Illustrative examples are tolyl, ethylphenyl, isopropylphenyl, tert-butylphenyl, sec-pentylphenyl, n-hexylphenyl, tert-octylphenyl, isononylphenyl or n-dodecylphenyl.

Any 5- to 7-membered heterocyclic ring metionend above may contain 1 or 2 a N- or O -atoms and is preferably a saturated ring, more preferably a 6-membered ring. Such a ring is typically the piperidine, hexamethyleneimine, piperazine or morpholine ring.

Alkylene of 1 to 12 carbon atoms can be typically methylene, ethylene, trimethylene, 2,2-dimethyl-1,3-propanediyl, tetramethylene, pentamethylene, hexamethylene, heptamethylene, octamethylene, decamethylene or dodecamethylene. Trimethylene, tetramethylene, hexamethylene and octamethylene are preferred.

Alkylene which is interrupted by oxygen atoms, preferably by 1 or 2 oxygen atoms, may be 3-oxapentane-1,5-diyl; 3,6-dioxaoctane-1,8-diyl; 2-oxapropane-1,3-diyl; 2,7-dioxaoctane-1,8—diyl or 2,6-dioxa-4,4-dimethyl-1,7-heptanediyl.

Alkenylene of 2 to 12 carbon atoms may contain one or more double bonds, preferably one double bond, and be straight-chain or branched. Illustrative examples of such alkenyl radicals are: vinylene, alkylene, 2-methalkylene, 2-hexenylene, 2-methyl-3-butenylene, 4-propyl-2-pentenylene, 2-decenylene or dodecenylene.

Alkenylene which is interrupted by 1 or 2 oxygen atoms may be 3-oxa-5-heptenylene, 2,7-dioxa-4-octenylene, 3,8-dioxa-5-decenylene or 3-oxa-5,8-undecadienylene.

Phenyl-$C_{14}$-alkyl and $C_7$–$C_9$-Phenylalkyl can be benzyl, phenethyl, 3-phenylpropyl, a-methylbenzyl und a,a-dimethylbenzyl. Benzyl is preferred.

The compounds of the invention can be produced by known methods, as described, for example in J. Chem. Soc 1934,1678, U.S. Pat. No. 5,422,847, GB-A-2062888, DE-A-3221883 and GB-A-2077455.

Examples of compounds of formula I are:
A1
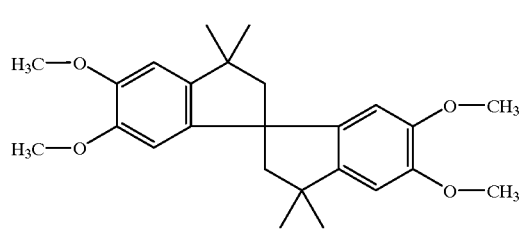
A2
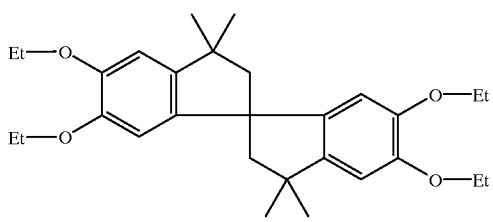
A3
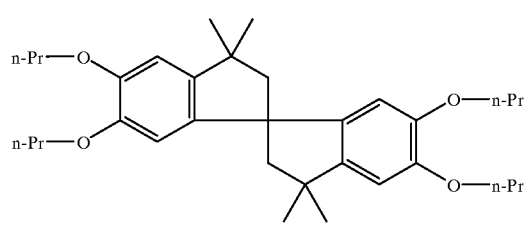
A4
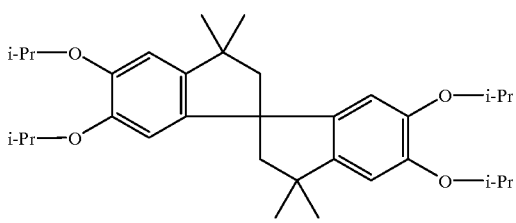
A5
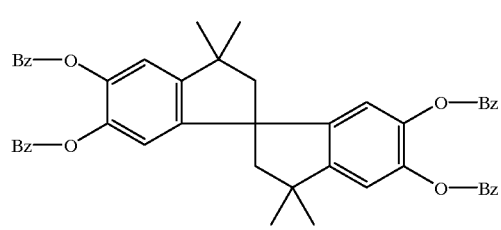
A6
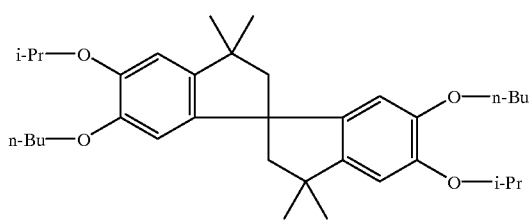
A7
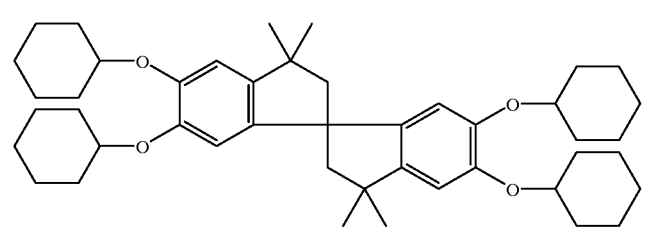
A8
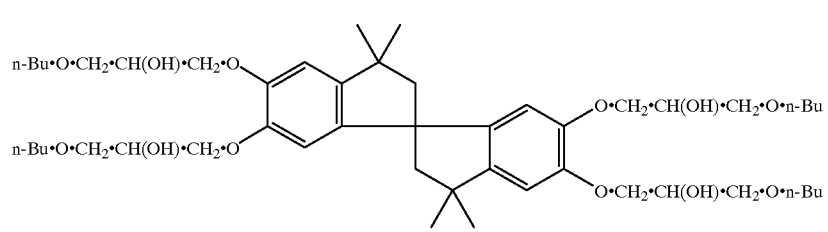
A9
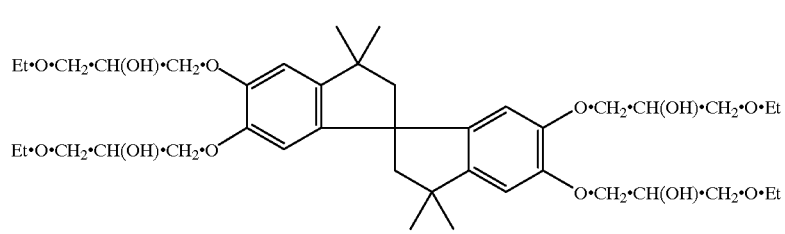

-continued
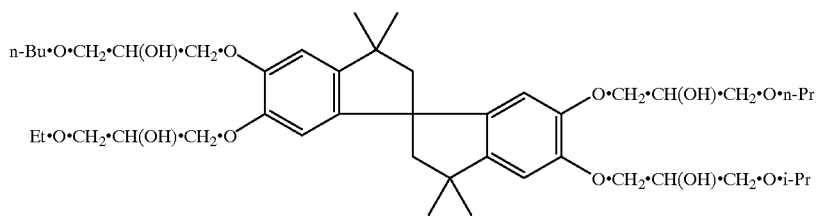
A10
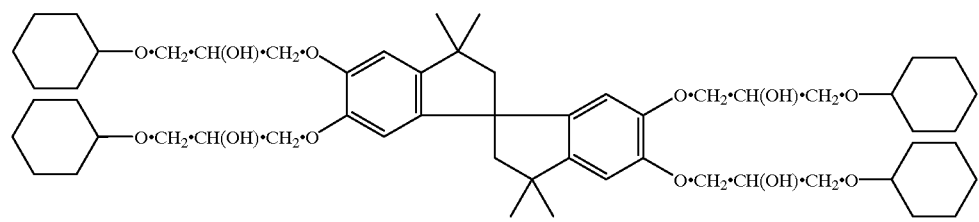
A11
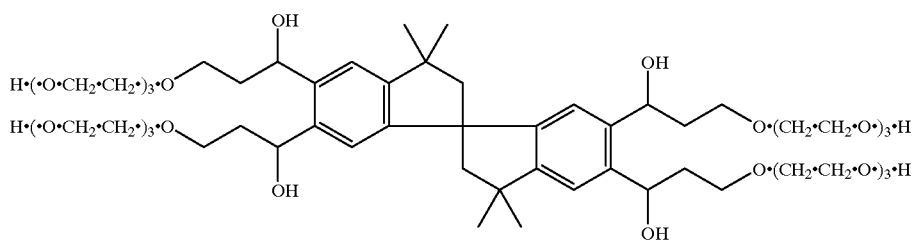
A12
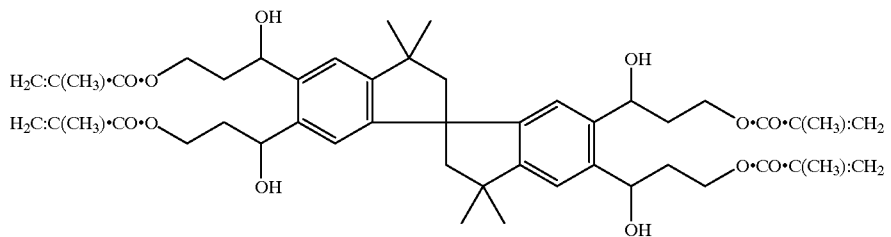
A13
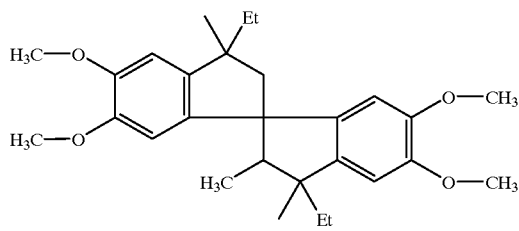
A15
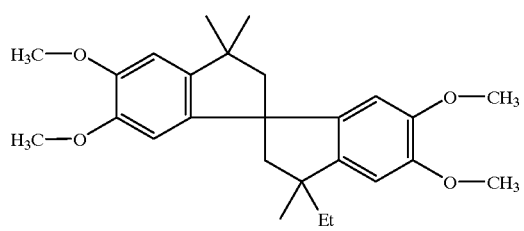
A16
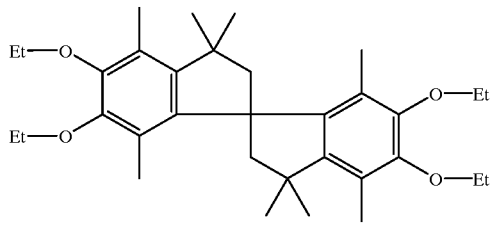
A17
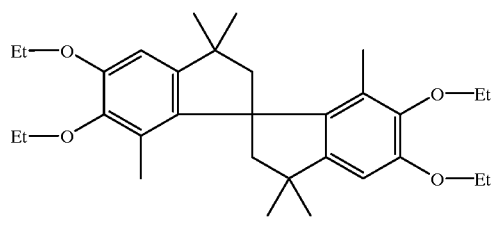
A18

-continued

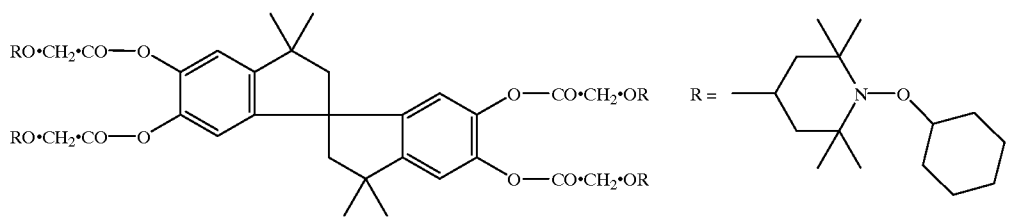

A19

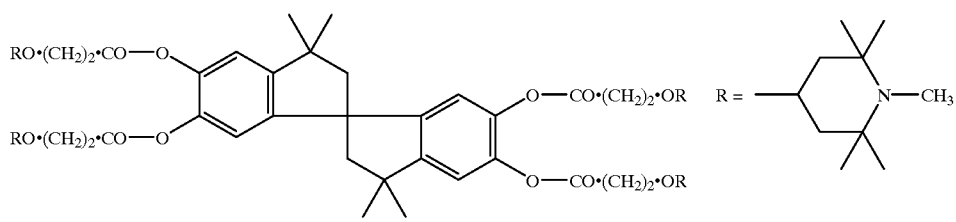

A20

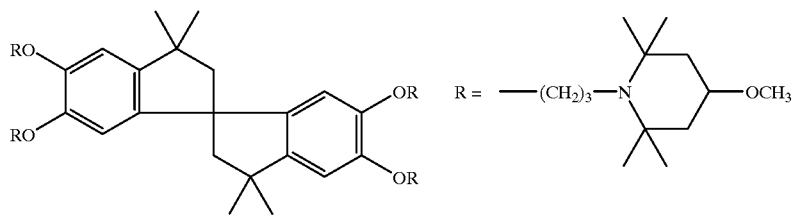

A21

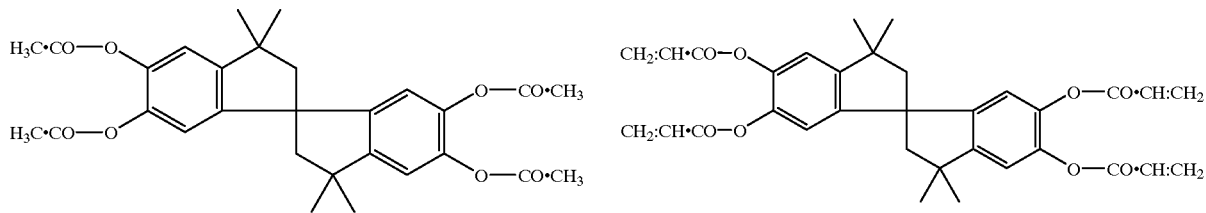

A22    A23

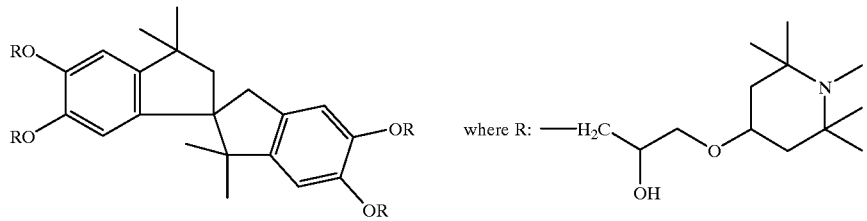

A24

Abbreviations:

Et=Ethyl, Pr=Propyl, Bu=Butyl, Bz=Benzyl

The invention relates also to novel compounds of formula I as described above, in which at least one of $R_1$ to $R_4$ is a group i), j) or k) wherein $R_{17}$ is a group

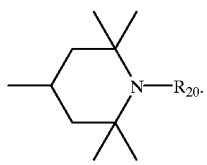

The spiroindane derivatives generally do not stabilise against oxidation by air, but are very effective in preventing attack by $NO_x$. This effect has nowhere been described in the literature. They also do not yellow in the presence of $NO_x$.

The combination of a spiroindane derivative and a phosphite therefore offers the first effective solution to the problem of discoloration caused by attack of $NO_x$ on (aromatic) components of paint binders.

The spiroindane derivatives are resistant to oxidation, non-volatile, thermally stable, readily soluble, colourless and can be easily manufactured from cheap starting materials (acetone+catechol). For use in powder coatings there is a general limitation which concerns compounds having a high melting point. The compounds of the invention with the appropriate substituion, as illustrated by examples A1 to A24, have a conveniently low melting point.

The novel coating composition preferably comprises 0.01–10 parts by weight of B, in particular 0.05–10 parts by weight of B, especially 0.1–5 parts by weight of B, per 100 parts by weight of solid paint or coating material A.

Multilayer systems are also possible here, where the concentration of the stabilizer (component B) in the outer layer can be higher, for example from 1 to 15 parts by weight of B, especially 3–10 parts by weight of B, per 100 parts by weight of solid component A.

The use of the novel mixture as stabilizer in coatings has the additional advantage that delamination, i.e. peeling-off of the coating from the substrate, is prevented. This advantage is particularly important in the case of metallic substrates, including in the case of multilayer systems on metallic substrates.

The binder can in principle be any binder which is customary in industry, for example those as described in Ullmann's Encyclopedia of Industrial Chemistry, 5thEdn., Vol.A18, pp.368–426, VCH, Weinheim, 1991. In general, this is a film-forming binder based on a thermoplastic or thermosetting resin, predominantly based on a thermosetting resin. Examples thereof are alkyd, acrylic, polyester, phenolic, melamine, epoxy and polyurethane resins and mixtures thereof.

The binder can be cold-curable or hot-curable; it may be advantageous to add a curing catalyst. Suitable catalysts which accelerate curing of the binder are described, for example, in Ullmann's Encyclopedia of Industrial Chemistry, Vol.A18, p.469, VCH Verlagsgesellschaft, Weinheim, 1991.

Preference is given to coating compositions in which component A contains a binder comprising a functional acrylate resin and a crosslinking agent.

Examples of coating compositions containing specific binders are:
1. Paints based on cold- or hot-crosslinkable alkyd, acrylate, polyester, epoxy or melamine resins, or mixtures of such resins, if desired with addition of a curing catalyst;
2. Two-component polyurethane paints based on hydroxyl-containing acrylate, polyester or polyether resins and aliphatic or aromatic isocyanates, isocyanurates or polyisocyanates;
3. One-component polyurethane paints based on blocked isocyanates, isocyanurates or polyisocyanates which are deblocked during baking;
4. Two-component paints based on (poly)ketimines and aliphatic or aromatic isocyanates, isocyanurates or polyisocyanates;
5. Two-component paints based on (poly)ketimines and an unsaturated acrylate resin or a polyacetoacetate resin or a methacrylamidoglycolate methyl ester;
6. Two-component paints based on carboxyl- or amino-containing polyacrylates and polyepoxides;
7. Two-component paints based on anydride-containing acrylate resins and a polyhydroxyl or polyamino component;
8. Two-component paints based on acrylate-containing anhydrides and polyepoxides;
9. Two-component paints based on (poly)oxazolines and anhydride-containing acrylate resins or unsaturated acrylate resins or aliphatic or aromatic isocyanates, isocyanurates or polyisocyanates;
10. Two-component paints based on unsaturated polyacrylates and polymalonates;
11. Thermoplastic polyacrylate paints based on thermoplastic acrylate resins or externally crosslinking acrylate resins in combination with etherified melamine resins;
12. Paint systems based on siloxane-modified or fluorine-modified acrylate resins.

In addition to components A and B, the novel coating composition preferably comprises, as component C, a phosphite compound. In addition to components A, B and, if used, C, the coating composition can comprise further components, for example solvents, pigments, dyes, plasticizers, stabilizers, thixotropic agents, drying catalysts and/or flow-control agents. Examples of possible components are those as described in Ullmann's Encyclopedia of Industrial Chemistry, 5thEdn., Vol.A18, pp.429–471, VCH, Weinheim, 1991.

Possible drying catalysts or curing catalysts are, for example, organometallic compounds, amines, amino-containing resins and/or phosphines. Examples of organometallic compounds are metal carboxylates, in particular those of the metals Pb, Mn, Co, Zn, Zr and Cu, or metal chelates, in particular those of the metals Al, Ti and Zr, or organometallic compounds, for example organotin compounds.

Examples of metal carboxylates are the stearates of Pb, Mn and Zn, the octanoates of Co, Zn and Cu, the naphthenates of Mn and Co and the corresponding linoleates, resinates and tallates.

Examples of metal chelates are the aluminium, titanium and zirconium chelates of acetylacetone, ethyl acetylacetate, salicyl aldehyde, salicyl aldoxime, o-hydroxyacetophenone and ethyl trifluoroacetylacetate, and the alkoxides of these metals.

Examples of organotin compounds are dibutyltin oxide, dibutyltin dilaurate and dibutyltin dioctanoate.

Examples of amines are in particular tertiary amines, for example tributylamine, triethanolamine, N-methyldiethanolamine, N-dimethylethanolamine, N-ethylmorpholine, N-methylmorpholine and diazabicyclooctane (triethylenediamine) and salts thereof. Further examples are quaternary ammonium salts, for example trimethylbenzylammonium chloride.

Amino-containing resins are simultaneously binder and curing catalyst. Examples thereof are amino-containing acrylate copolymers.

The curing catalyst can also be a phosphine, for example triphenylphosphine.

The novel coating compositions can also be radiation-curable. In this case, the binder essentially comprises monomeric or oligomeric compounds containing ethylenically unsaturated bonds which are cured, after application, by actinic radiation, i.e. are converted into a crosslinked, high-molecular-weight form. UV-curing systems generally additionally contain a photoinitiator. Corresponding systems are described in the abovementioned publication, Ullmann's Encyclopedia of Industrial Chemistry, 5thEdn. Vol.A18, pages 451–453. In radiation-curable coating compositions, the novel stabilizer mixtures can also be employed without addition of sterically hindered amines.

The novel coating compositions can be applied to any desired substrates, for example to metal, wood, plastic or ceramic materials. The stabilizers of the invention are used preferably in systems subjected to high temperatures, such as powder paints and coil coatings, but also in systems in which the needs to prevent discoloration are great, such as in top coats.

The novel coating compositions can be applied to the substrates by conventional processes, for example by brushing, spraying, pouring, dipping or electrophoresis; see also Ullmann's Encyclopedia of Industrial Chemistry, 5thEdn., Vol.A18, pp. 491–500.

The curing of the coatings can—depending on the binder system—be carried out at room temperature or by warming. The coatings are preferably cured at 50–150° C., powder coatings usually at higher temperatures, and coil coatings at temperatures up to as much as 300° C.

The coatings obtained in accordance with the invention have excellent resistance to the harmful effects of oxygen and heat.

The invention therefore also relates to a coating, in particular a paint, which has been stabilized against the harmful effects of light, oxygen and heat by a content of the novel mixture comprising compounds of the formula 1. The paint is preferably a top coat for automobiles, a powder paint or a coil coating. The invention furthermore relates to a process for stabilizing a coating based on organic polymers against damage by light, oxygen and/or heat, which comprises admixing a mixture comprising a compound of the formula I and a compound of the formula 11 with the coating composition, and to the use of a mixture comprising compounds of formula I in coating compositions as stabilizers against damage by light, oxygen and/or heat.

The coating compositions can comprise an organic solvent or solvent mixture in which the binder is soluble. However, the coating composition can also be an aqueous solution or dispersion. The vehicle can also be a mixture of an organic solvent and water. The coating composition can also be a high-solids paint or contain no solvent (powder paint).

The pigments can be inorganic, organic or metallic pigments. The novel coating compositions preferably contain no pigments and are used as clear coats.

Likewise preferred is the use of the coating composition as top coat for applications in the automobile industry, in particular as a pigmented or unpigmented top coat of the finish. However, use for underlying layers is also possible.

Coating compositions usually consist of binders, additives and, optionally, chromophoric components.

Suitable binders are in principle all those customary in the art, for example those described in Ullmann's Encyclopedia of Industrial Chemistry, 5. Ed., Vol. A18, pp. 368–426, VCH, Weinheim 1991. The binder is usually a film-forming binder based on a thermoplastic or thermocurable resin, preferably on a thermocurable resin. Typical examples are alkyd resins, acrylic resins, polyester resins, phenolic resins, melamine resins, epoxy resins, polyurethane resins and mixtures thereof.

The binder may be a cold-curable or hot-curable binder and the addition of a curing catalyst may be advantageous. Suitable catalysts which accelerate the full cure of the binder are described, inter alia, in Ullmann's Encyclopedia of Industrial Chemistry, Vol. A18, p.469, VCH Verlagsgesellschaft, Weinheim 1991.

Preferred coating compositions are those containing as film-forming binder epoxy resins, polyurethane resins, polyester resins, acrylic resins and the copolymer resins thereof, polyvinyl resins, phenolic resins, alkyd resins or mixtures of such resins.

If the novel compositions are coating compositions or paint systems, then these may contain further customary components, typically selected from the group consisting of the dyes, pigments, fillers, flow control agents, adhesion promoters, curing catalysts, light stabilisers or antioxidants.

The compounds are used preferably alone and mixed together with other stabilisers in liquid and powder paints.

For use in powder coatings, solid compounds with melting points in the range 50–100° C. are strongly preferred for reason of their ease of handling and for their easier incorporation during extrusion. An example of such a compound having good activity and a suitable melting point (80° C.) is:

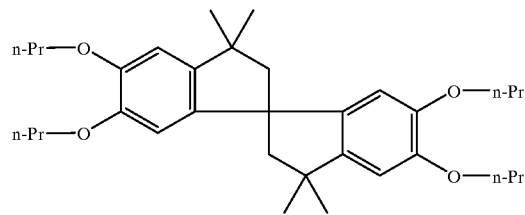

The compounds of the formula I are known and their preparation is described, for example, in U.S. Pat. No. 4,612,049. Their use in powder coatings is a particularly preferred field where the invention is useful.

Interest attaches to powder coatings comprising as component (ii) at least one calcium-modified silicate pigment in which the calcium content is from 2 to 7% by weight.

The definition of "powder coatings" is understood to be that as described in Ullmann's Encyclopedia of Industrial Chemistry, 5th, Completely Revised Edition, Vol. A 18, pages 438 to 444 (1991) in Section 3.4. Powder coatings are understood as thermoplastic or stovable, crosslinkable polymers which are applied in powder form to predominantly metallic substrates. The manner in which the powder is brought into contact with the workpiece to be coated characterizes the various application techniques, such as, for example, electrostatic powder spraying, electrostatic fluidized-bed sintering, bed sintering, fluidized-bed sintering, rotational sintering or centrifugal sintering.

Preferred organic film-forming binders for the powder coating composition according to the invention are stoving systems based on, for example, epoxy resins, polyester resins, epoxy-polyester resins, polyester cured with hydroxyalkylamides, glycol . . . triglycidyl isocyanurate, aliphathic polyoxciranes,uretdiones, blocked polyisocyanates, polyurethane resins, polyester-polyurethane resins, acrylate resins or mixtures of such resins. Also of interest are film-forming binders with thermoplastic properties, examples being polyethylene, polypropylene, polyamides, polyvinyl chloride, polyvinylidene dichloride or polyvinylidene difluoride. Furthermore, powder coatings are also known which comprise ethylenically unsaturated components and can be cured with photoinitiators.

Polyesters are in general hydroxy-functional or carboxy-functional and are commonly prepared by condensation of diols and dicarboxylic acids. By adding polyols and/or polyacids, branched polyesters are obtained which then, on stoving in the presence of crosslinking agents, give rise to network structures which give the coating the desired physical properties, such as scratch resistance, impact resistance and flexural strength. In place of polyfunctional acids it is also possible to use anhydrides or acid chlorides, for example maleic anhydride, itaconic anhydride, phthalic anhydride, terephthalic anhydride, hexahydroterephthalic anhydride, trimellitic anhydride, pyromellitic dianhydride, succinic anhydride, etc. It is also possible to use simple esters, for example dimethyl terephthalate, in which case polymerization takes place by transesterification with elimination of the volatile alcohol. Likewise practicable is preparation by combination of transesterification and condensation. Furthermore, polyesters can be prepared by polycondensation of hydroxycarboxylic acids, for example 12-hydroxystearic acid and hydroxypivalic acid, or of the corresponding lactones, for example ε-caprolactone. Examples of dicarboxylic acids and polyacids include terephthalic acid, isophthalic acid, adipic acid, azelaic acid, sebacic acid, 1,12-dodecanedioic acid, pyromellitic acid, 3,6-dichlorophthalic acid, succinic acid, 1,3-cyclohexanedicarboxylic acid and 1,4-cyclohexanedicarboxylic acid. Examples of diols and polyols include ethylene glycol, propylene glycol, glycerol, hexanetriol, hexane-2,5-diol, hexane-1,6-diol, pentaerythritol, sorbitol, neopentylglycol, trimethylolethane, trimethylolpropane, tris-1,4-cyclohexanedimethanol, trimethylpentanediol, 2,2-diethyl-1,3-propanediol, 2-methyl-2-butyl-1,3-propanediol, ester diol 204 (ester of hydroxypivalic acid and neopentylglycol), hydrogenated bisphenol A, bisphenol A, hydroxypivalic acid, hydroxypivalate esters, 2-butyl-2-ethyl-1,3-propanediol, 1,4-butanediol, 2-butene-1,4-diol, 2-butyne-1,4-diol or 2-methyl-1,3-propanediol.

Suitable crosslinking agents for carboxy-functional polyesters are epoxy compounds, such as, for example, novolak-epoxy resins, diglycidyl ethers of bisphenol A, hydrogenated bisphenol A, and bisphenol A modified by reaction with, for example, aliphatic dicarboxylic acids. Also suitable are reactive epoxy compounds, such as triglycidyltriazolidine-3,5-dione, the glycidyl esters of polyacids, for example diglycidyl terephthalate and diglycidyl hexahydroterephthalate, hydantoin epoxides (U.S. Pat. No. 4,402,983) and, very particularly, triglycidyl isocyanurate and Araldit® PT910 (Ciba-Geigy). Other crosslinking agents for carboxy-functional polyesters are β-hydroxyalkylamides (U.S. Pat. No. 4,076,917), for example the predominantly tetrafunctional β-hydroxyalkylamide derivative of adipic acid (Primid® XL552 from Rohm & Haas). Others which have proven suitable include derivatives of melamine, benzoguanimine and glycoluril, which are alkylated with low molecular weight alcohols. Examples are tetramethylmethoxyglycoluril (Powderlink® 1174 from American Cyanamid). Other known cross-linking agents are bis- and trisoxazolidines, for example 1,4-bisoxazolidinobenzene. In comparison with systems crosslinked using tetramethylmethoxyglycoluril or β-hydroxyalkylamide derivatives of adipic acid, coatings containing triglycidyl isocyanurate as crosslinking agent are of greater corrosion resistance. The former systems tend to be less corrosion-resistant, which is possibly a result of the hydrophilicity of the crosslinking agent. In such systems, the compounds of the present invention are of particular interest as corrosion inhibitors.

A recent development comprises carboxy-functional polyesters which contain chemically bonded epoxy groups and are consequently able to crosslink with themselves (Molhoek et al., 22nd Fatipec Congress, 15.–19.5.95, Budapest, Vol.1, 119–132).

In all systems in which an epoxy group or a glycidyl radical reacts with a carboxyl group or an anhydride in a crosslinking reaction, catalysts can be employed. Examples are amines or metal compounds, for example aluminium acetylacetonate or tin octoate.

As crosslinking agents for hydroxyfunctional polyesters, the polyisocyanate crosslinkers are of particular importance. In order to prevent premature crosslinking because of the high reactivity of isocyanates, and in order to obtain good levelling of the melted powder, the polyisocyanates are blocked (internally as a uretdione or as an adduct with a blocking agent). The most frequently employed blocking agents are ε-caprolactam, methyl ethyl ketoxime or butanoneoxime. Other suitable blocking agents for isocyanates are described in the publications of G. B. Guise, G. N. Freeland and G. C. Smith, J. Applied Polymer Science, 23, 353 (1979) and of M.Bock and H. -U. Maier-Westhues in "Progress in Product Development for Powder Coating Technology", XIX th Int. Conf. on Organic Coatings, Science and Technol., Athens, Jul. 12–16, 1993. Examples of blocked or unblocked polyisocyanates include 2-methylpentane-1,5-diisocyanate, 2-ethylbutane-1,4-diisocyanate, 3(4)-isocyanatomethyl-1-methylcyclohexyl isocyanate, 3-isocyanatomethyl-3,5,5-trimethylcyclohexane diisocyanate, tris(isocyanatomethyl)benzene, 4,4'-diisocyanatodicyclohexylmethane, 1,4-bis-(isocyanatomethyl)cyclohexane, m-tetramethylxylene diisocyanate, p-tetramethylxylene diisocyanate and, in particular, isophorone diisocyanate. For the purpose of deblocking, a metallic catalyst, for example tin octoate, dibutyltin oxide or dibutyltin dilaurate, is usually added to the polyisocyanate formulation.

Other crosslinking agents suitable for hydroxy-functional polyesters are anhydrides, for example trimellitic anhydride and its reaction products with diols and diamines. Further examples of such crosslinking agents are described by T. A. Misev in "Powder Coatings: Chemistry and Technology", J.Wiley & Sons, Chichester on pages 123 and 124.

Polyacrylates, which usually have hydroxy, carboxy or glycidyl functionality, are also employed as binders for powder coatings. They are prepared by the customary methods, predominantly from monomers such as styrene and linear or branched $C_1$–$C_8$ alkyl esters of acrylic acid or methacrylic acid. Other ethylenically unsaturated compounds, for example divinylbenzene, acrylamide, methacrylamide, butoxymethylacrylamide, acrylonitrile, butadiene, etc., can also be added and copolymerized. Hydroxy functionality is provided by the copolymerization of hydroxy-functional monomers such as, for example, hydroxyethyl acrylate, hydroxyethyl methacrylate, hydroxypropyl acrylate and hydroxypropyl methacrylate. For carboxy functionality, ethylenically unsaturated acids and anhydrides, for example acrylic acid, methacrylic acid, itaconic acid, crotonic acid, maleic anhydride, itaconic anhydride, acrylic anhydride or methacrylic anhydride are used (U.S. Pat. No. 3,836,604). Glycidyl functionality is provided, as taught in EP-A-0 256 369 and U.S. Pat. No. 3,876,578, by the copolymerization of monomers such as glycidyl acrylate and glycidyl methacrylate. As crosslinking agents for polyacrylates with hydroxy or carboxy functionality it is in principle possible to use the same compounds as already described for the polyesters with hydroxy or carboxy functionality. Further suitable crosslinking agents are the epoxy compounds of U.S. Pat. No. 0,040,040. Suitable crosslinking agents for polyacrylates with glycidyl functionality are dicarboxylic acids such as, for example, sebacic acid and 1,12-dodecanedioic acid, and anhydrides, for example bistrimellitic anhydride and the compounds described in U.S. Pat. No. 3,880,946. Also known, furthermore, are autocrosslinking polyacrylates, from DE-A-3 310 545.

Epoxy resins for powder coatings are mostly either novolak-epoxy resins or, in particular, those based on aromatic polyols, especially on bisphenols such as bisphenol A. Also known are modified bisphenol-epoxy resins from JP-A-58 187 464 (1982). The epoxy resins are employed in combination with crosslinking agents from the classes of the solid aliphatic amines, solid aromatic amines, amine adducts, phenolic resins, polyacids and the already described carboxyfunctional polyesters. Hardeners (curing agents) meriting special mention are the dicyandiamides, which are frequently employed together with a catalyst such as, for example, Lewis acids, boron trifluoride amine complexes, metal complexes, tertiary or quaternary amines, and imidazoline derivatives such as 2-methylimidazoline.

The powder coating compositions can in addition comprise one or more components from the group consisting of pigments, dyes, fillers, levelling assistants, degassing agents, charge control agents, optical brighteners, adhesion promoters, antioxidants, light stabilizers, curing catalysts and photoinitiators. They can also contain other known anticorrosion agents, for example anticorrosion pigments, such as phosphate- or borate-containing pigments or metal oxide pigments, or other organic or inorganic corrosion inhibitors, for example salts of nitroisophthalic acid, phosphoric esters, technical-grade amines or substituted benzotriazoles.

Suitable photoinitiators are those based on benzophenones, phenyl glyoxalates, bis- or mono-acylphosphine oxides, a-hydroxy ketones or benzyl dimethyl ketals.

The pigments are for example titanium dioxide, iron oxide, carbon black, aluminium bronze or phthalocyanine blue.

Examples of fillers are talc, alumina, aluminium silicate, barytes, mica or silica. The corrosion inhibitors can also be applied to pulverulent carrier materials.

Examples of degassing agents are fatty acid amides as described in EP-A-0 471 409, ε-caprolactam, methyl isophthalate and dimethyl isophthalate (EP-A-284 996), and especially benzoin.

Examples of levelling assistants are epoxidized fatty acids, abietyl alcohol, polylauryl methacrylate, polylauryl acrylate, polydimethylsiloxane-polyalkylene oxide block copolymers or, in particular, low molecular weight copolymers and polymers of $C_1$–$C_8$alkyl acrylate esters or alkyl methacrylate esters.

Adhesion promoters are based, for example, on modified silanes, titanates or zirconates.

It is also advantageous to add basic fillers or pigments, which in certain binder systems bring about a synergistic effect on the inhibition of corrosion. Examples of such basic fillers and pigments are calcium carbonate or magnesium carbonate, zinc oxide, zinc carbonate, zinc phosphate, magnesium oxide, alumina, aluminium phosphate, or mixtures thereof. Examples of basic organic pigments are those based on am-inoanthraquinone.

In the case of the preparation of the organic film-forming binder by polymerization or polycondensation of monomers the spiroindane compound (i) can be admixed to the monomers even prior to polymerization.

The spriroindane compounds are expediently used in a quantity of from 0.05 to 10% by weight, preferably from 0.1 to 10% by weight, in particular from 0.1 to 2% by weight, based on the weight of the total solids of the powder coating composition.

In addition to the already mentioned phosphites further conventional additives may be present in the paint compositions.

Examples of conventional additives are:
UV absorbers and light stabilisers
1.2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl) benzotriazole, 2-(2'-hydroxy-4'-octyloxyphenyl) benzotriazole, 2-(3',5'-di-tert-amyl-2'-hydroxyphenyl) benzotriazole, 2-(3',5'-bis(a,a-dimethylbenzyl)-2'-hydroxyphenyl)benzotriazole, mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl) phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl) benzotriazole, 2-(3'-tert-butyl-5'-[2-(2-ethylhexyloxy) carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl) phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol300;

where R=3'-tert-butyl-4'-hydroxy-5'-2H-benzotriazol-2-ylphenyl.

2.2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

3. Esters of substituted and unsubstituted benzoic acids, as for example 4-tert-butylphenyl salicylate, phenyl salicylate, octylphenyl salicylate, dibenzoyl resorcinol, bis(4-tert-butylbenzoyl) resorcinol, benzoyl resorcinol, 2,4-di-tertbutylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

4. Acrylates, for example ethyl a-cyano-b,b-diphenylacrylate, isooctyl a-cyano-b,b-diphenylacrylate, methyl a-carbomethoxycinnamate, methyl a-cyano-b-methyl-p-methoxy-cinnamate, butyl a-cyano-b-methyl-p-methoxy-cinnamate, methyl a-carbomethoxy-p-methoxycinnamate and N-(b-carbomethoxy-b-cyanovinyl)-2-methylindoline.

5. Nickel compounds, for example nickel complexes of 2,2'-thio-bis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyi-5-hydroxypyrazole, with or without additional ligands.

6. Sterically hindered amines, for example bis(2,2,6,6-tetramethylpiperidyl)sebacate, bis-(2,2,6,6-tetramethylpiperidyl)succinate, bis(1,2,2,6,6-pentamethylpiperidyl)sebacate, bis-(1,2,2,6,6-pentamethylpiperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl)hexamethylenediamine and 4-tertoctylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butane-tetracarboxylate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6- pentamethypiperidyl)-2-n-butyl-2-(2-hydroxy-3,5-di-tert-butylbenzyl)malonate, 3-n-octyl-7,7,9,9-tetramethyl-1,3,8-triazaspiro[4.5]-decan-2,4-dion, bis(1-octyloxy-2,2,6,6-tetramethylpiperidyl)sebacate, bis(1-octyloxy-2,2,6,6-tetramethylpiperidyl)succinate, the condensate of N,N'-bis (2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl )-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl) pyrrolidin-2,5-dione, 3-dodecyl-1-(1,2,2,6,6-pentamethyl-4-piperidyl)pyrrolidine-2,5-dione.

7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxyanilide and its mixture with 2-ethoxy-2'-ethyl-5,4'-di-tert-butoxanilide and mixtures of ortho- and paramethoxy-disubstituted oxanilides and mixtures of o- and p-ethoxy-disubstituted oxanilides.

8. 2-(2-Hydroxyphenyl)-1.3.5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2-hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenyl hydrazide, N,N'-diacetyladipoyl dihydrazide, N,N'-bis(salicyloyl) oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl) methylphosphite, bis(2,4-di-tert-butyl-6-methylphenyl) ethyl phosphite.

5. Peroxide scavengers, for example esters of b-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(b-dodecylmercapto)propionate.

6. Polyamide stabilisers, for example, copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or tin pyrocatecholate.

8. Nucleating agents, for example, 4-tert-butylbenzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxides, carbon black, graphite.

10. Other additives, for example, plasticisers, lubricants, waxes, slip agents, emulsifiers, pigments, optical brighteners, flameproofing agents, antistatic agents, biocides and blowing agents.

The following Applications Examples will illustrate the invention without limiting the scope thereof.

EXAMPLE 1

A typical epoxy/polyester powder coating composition was made up, but for ease of handling was dissolved in solvent and coated from solution. The polyester was a commercially available carboxy-functionalised type, having an acid value of 70–85 and was free from added antioxidants.

| | |
|---|---|
| Polyester (50/50 type) | 491 parts by wt. |
| Araldite ® GT 7004 (Ciba-Geigy AG.)[1] | 491 |
| Resiflow ® PV88 (Worleé Chemicals)[2] | 15 |
| Benzoin (Fluka AG) | 3 |
| TiO$_2$ Bayer type R-KB-5 | 500 |
| Total solids | 1500 |
| Dichloromethane puriss | 1800 |
| Acetone puriss | 450 |
| Fluorad ® FC170C (3 M Co.)[3] | 7.5 |
| Total | 3757.5 |

The powder coating components were dissolved up in the solvent mix using a high speed (dissolver. 35 g portions of the coating liquid were added to 0.0467g of the additives to be tested in a screw-cap bottle. The contents were dissolved up, degassed under vacuum and the weight readjusted with fresh dichloromethane before coating at 150 μm wet coating weight onto coil-coated aluminium. The coatings, after drying, were all of thickness 51±3 μm and contained a total of 0.5% additives (on resin).

To cure the coatings, a gas reactor was used. The gas reactor is a flat plate of thermally-annealed stainless steel (to avoid distortion on heating) having a shallow cavity in the middle and sealed by a heavy, removable stainless steel lid. At one end, a preheated mixture of approximately 80 ppm NO$_2$ in air was passed into the block, flowed both over and under the test samples and was allowed to escape at the other end. The gas reactor was placed in an electric ovenset at 200° C., on a thermally insulating support. The coatings were cured for 15 mins. and overbaked for 15 minutes using this simple apparatus. After curing and overbaking the yellowness index was measured using a Macbeth colour analyser. A high value of the yellowness index denotes greater yellowness of the test panel.

The following results were obtained:

| Additive(s) | Yellowness Index after ... at 200° C. | |
|---|---|---|
| | 15 minutes | 15 + 45 minutes |
| No additive | 6.3 | 20.8 |
| Tris-(2,3-di-tert. butyl phenyl)-phosphite | 6.2 | 20.2 |
| 1:1 mixture of pentaerthrityl-tetrakis[3-3,5-di-tert.butyl-4-hydroxyphenyl)-propionate] and tris-(2,3-di-tert. butyl phenyl)-phosphite | 7.7 | 18.7 |
| Compound A3 | 5.8 | 16.2 |
| 1:2 mixture of compound A3 with tris-(2,3-di-tert. butyl phenyl)-phosphite | 5.7 | 16.6 |

EXAMPLE 2

In order to demonstrate that the compounds of the invention are effective in a typical epoxy/polyester powder coating, the following formulations were mixed together in a planetary mixer.

| Component | Formulation Quantities in grams | | | |
|---|---|---|---|---|
| | 1 | 2 | 3 | 4 |
| Crylcoat ® 360 (UCB Chemicals SA)[4] | 473 | 473 | 473 | 473 |
| Araldite GT 7004 (Ciba-Geigy AG.)[1] | 315 | 315 | 315 | 315 |
| Resiflow PV88 (Worleé Chemicals)[2] | 9.6 | 9.6 | 9.6 | 9.6 |
| Benzoin (Fluka AG) | 2.4 | 2.4 | 2.4 | 2.4 |
| $TiO_2$ Bayer type R-KB-5 | 400 | 400 | 400 | 400 |
| Irganox B225 ® (1:1 mixture of pentaerthrityl-tetrakis-[3-3,5-di-tert.butyl-4-hydroxyphenyl)-propionate] and tris-(2,3-di-tert. butyl phenyl)-phosphite) (Ciba-Geigy AG) | — | 1.2 | — | — |
| Compound A3 | — | — | 1.2 | 0.4 |
| Phosphorous acid, bis[2,4-bis(1,1-dimethylethyl)-6-methylphenyl] ethyl ester | — | — | — | 0.8 |

The formulations were extruded twice using a Buss PLK46L cokneader at 40 and 80° C. in zones 1 and 2 respectively and 125 rpm. The extrudate was cooled, crushed, milled in a Retsch M-1 ultracentrifugal mill at speed setting 2 with a 0.75 mm sieve and finally sieved through a 125 m•$10^{-6}$ gyratory sieve. The resultant powder had a mean particle size of 32 m•$10^{-6}$.

The powder paint was applied to white coil-coated aluminium panels with an ESB-Wagner Airmatic Corona-Star type PEM-CG1 gun (with a low output of free electrons) to give coatings of thickness ca. 120 m•$10^{-6}$. The powder was not cured, but briefly fused by a heat treatment of 30 seconds at 160° C. in air.

Samples of the coatings were cured by heating 15 mins at 195° C. in pure air and in the previousy-described gas reactor in an air/80 ppm $NO_2$ mixture. The yellowness index was measured using a Macbeth colour analyser after fusing the powder and after baking: from these values the yellowness index differences were calculated.

The following results were obtained:

| Formulation | Description | Δ Yellowness Index on curing | |
|---|---|---|---|
| | | in air | in air + 80 ppm $NO_2$ |
| 1 | No additive | 1.4 | 2.1 |
| 2 | State-of-the-art | 1.1 | 5.3 |
| 3 | Invention | 1.1 | 2.0 |
| 4 | Invention | 1.0 | 1.8 |

It can be seen that the state-of-the-art stabilisers give unsatisfactory yellowing as soon as traces of nitrogen oxides are present and that the compounds of the invention give better stabilisation, ie. smaller increments in the yellowness index.

What is claimed is:
1. A composition comprising
   (A) a powder coating material
   (B) at least one compound of formula

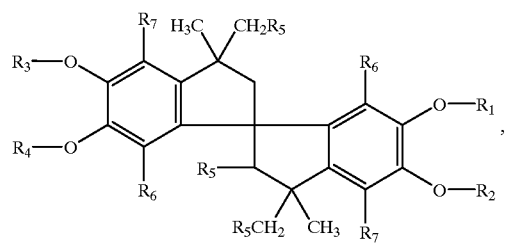

(I)

wherein $R_1$, $R_2$, $R_3$ and $R_4$ are independently of one another:
  a) unsubstituted $C_1$–$C_{18}$alkyl or $C_1$–$C_{18}$alkyl substituted by one or more of the groups OH, $C_1$–$C_{18}$alkoxy, $C_2$–$C_{18}$alkenyloxy, halogen, phenoxy (which is unsubstituted or substituted by $C_1$–$C_{18}$alkyl, $C_1$–$C_{18}$alkoxy or halogen), —$COOR_8$, —$CONH_2$, —$CONHR_9$ or —$CONR_9R_{10}$;
  b) $C_5$–$C_{12}$cycloalkyl which is unsubstituted or substituted by OH or —$OCOR_{11}$;
  c) a five or six-membered heterocycle that is saturated or unsaturated;
  d) $C_7$–$C_{11}$phenylalkyl, which is unsubstituted or substituted by one or more OH, Cl or $CH_3$;
  e) $C_2$–$C_{18}$alkenyl;
  f) $C_4$–$C_{30}$alkyl which is interrupted by one or more O atoms and can be substituted by OH;
  g) —CO—$R_{12}$ or —$(CH_2)_n$—CO—$R_{12}$,
  h) —$SO_2$—$R_{13}$;
  i) a group

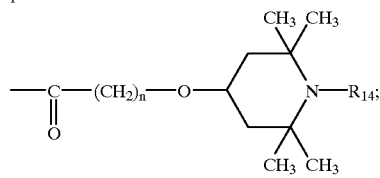

j) a group

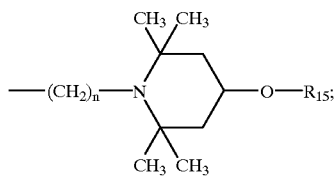

k) a group

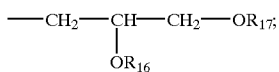

n is an integer between 1 and 18;

$R_5$ is H, $C_1$–$C_{18}$ straight chain or branched alkyl, $C_2$–$C_{18}$alkenyl or $C_6$–$C_{12}$aryl;

$R_6$ and $R_7$ are independently of one another H, halogen, $C_1$–$C_{18}$ alkyl, $C_2$–$C_6$alkenyl, $C_1$–$C_{12}$ alkoxy or $C_2$–$C_{12}$ alkenyloxy;

$R_8$ is $C_1$–$C_{18}$ alkyl, $C_2$–$C_{18}$alkenyl, $C_3$–$C_{20}$alkyl which is interrupted by one or more O, $NR_9$ or S and/or substituted by OH, $C_1$–$C_4$alkyl which is substituted by —P(O)($OR_{18}$)$_2$, $C_3$–$C_8$alkynyl or $C_7$–$C_{11}$phenylalkyl;

$R_9$ and $R_{10}$ are independently of one another $C_1$–$C_{12}$ alkyl, $C_3$–$C_{12}$alkoxyalkyl, $C_4$–$C_{16}$dialkylaminoalkyl or $C_5$–$C_{12}$ cycloalkyl, or $R_9$ and $R_{10}$ together are $C_3$–$C_9$ alkylene or $C_3$–$C_9$oxaalkylene or $C_3$–$C_9$azaalkylene;

$R_{11}$ is $C_1$–$C_{18}$ alkyl, $C_2$–$C_{18}$ alkenyl or phenyl;

$R_{12}$ is $C_1$–$C_{18}$alkyl, $C_1$–$C_{18}$alkenyl, phenyl, $C_1$–$C_{12}$alkoxy, phenoxy, $C_1$–$C_{12}$alkylamino or $C_6$–$C_{12}$arylamino or a group —$R_{19}$—COOH;

$R_{13}$ is $C_1$–$C_2$ alkyl, $C_6$–$C_2$ aryl or $C_7$–$C_{14}$ alkylphenyl;

$R_{14}$ is hydrogen, oxyl, hydroxy, —$CH_2CN$, $C_1$–$C_8$alkyl, –$C_{18}$alkoxy, $C_3$–$C_8$alkenyl, $C_3$–$C_8$alkynyl, $C_5$–$C_8$cycloalkyl or -alkoxy, phenyl, naphthyl, $C_7$–$C_{12}$phenylalkyl or -alkoxy, phenyl or phenylalkyl substituted by alkyl or phenyl of 7–14 carbon atoms, $C_3$–$C_5$alkenoyl, $C_1$–$C_{18}$alkynoyloxy, benzyloxy or a group $CH_2$—CH(OH)—Z where Z is H, $CH_3$ or phenyl, or a group of the formula

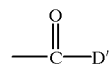

wherein D' is $C_1$–$C_{18}$alkyl, $C_1$–$C_{18}$ alkoxy, phenyl, or phenyl substituted by hydroxy, $C_1$–$C_8$alkyl, $C_1$–$C_{18}$alkoxy, amino or amino mono- or disubstituted by $C_1$–$C_8$alkyl or phenyl;

$R_{15}$ is H, $C_1$–$C_{18}$alkyl or $C_3$–$C_{18}$alkyl interrupted by one or more oxygen atoms; cyanoethyl, benzyl, glycidyl, a monovalent radical of an aliphatic, cycloaliphatic, araliphatic or aromatic carboxylic acid, or of carbamic acid, or of a phosphorus-containing acid, or a monovalent silyl radical —Si($R_{21}$)($R_{22}$)($R_{23}$);

$R_{16}$ is H, —CO—$R_{11}$, —Si($R_{21}$)($R_{22}$)($R_{23}$) or —$COOR_{24}$;

$R_{17}$ is $C_1$–$C_{18}$alkyl, $C_2$–$C_{18}$alkenyl, phenyl-$C_1$–$C_4$alkyl, $C_3$–$C_{24}$ alkyl or $C_2$–$C_{14}$hydroxyalkyl, each of which is interrupted by one or more O atoms, or is phenyl, which is unsubstituted or substituted by $C_1$–$C_4$ alkyl, $C_1$–$C_4$ alkoxy or halogen, $C_5$–$C_{12}$cycloalkyl which is unsubstituted or substituted by 1–3 $C_1$–$C_8$ alkyl, or —$COR_{11}$, or $R_{18}$ is $C_1$–$C_{18}$ alkyl or phenyl;

$R_{19}$ is $C_1$–$C_{18}$ alkylene, vinylene or phenylene;

$R_{20}$ is H, OH, oxyl, $C_1$–$C_{18}$alkyl, $C_2$–$C_{18}$alkenyl, $C_1$–$C_{18}$alkoxy, $C_5$–$C_{12}$cycloalkyl, $C_5$–$C_{12}$cycloalkoxy, $C_3$–$C_8$alkynyl, $C_7C_{12}$ phenylalkyl, $C_1$–$C_8$alkanoyl, $C_3$–$C_5$alkenoyl or glycidyl;

$R_{21}$, $R_{22}$ and $R_{23}$ are independently of one another $C_1$–$C_6$ alkyl or phenyl; and $R_{24}$ is $C_1$–$C_4$alkyl.

2. A composition according to claim 1 wherein in formula I $R_5$ is H;

$R_1$, $R_2$, $R_3$ and $R_4$ are the same and can be a) $C_1$–$C_{18}$ straight chain or branched alkyl, optionally substituted by one or more of the groups OH, $C_1$–$C_{18}$ alkoxy, $C_2$–$C_{18}$ alkenyloxy, —$COOR_8$, —$CONH_2$, —$CONHR_9$, —$CONR_9R_{10}$;

b) $C_5$–$C_{12}$ cycloalkyl which is unsubstituted or substituted by OH or —$OCOR_{11}$;

c) tetrahydropyranyl;

e) $C_2$–$C_{18}$ alkenyl;

f) $C_4$–$C_{30}$ alkyl which is interrupted by one or more O atoms and can be substituted by OH;

g) —O—$R_{12}$ or —($CH_2$)$_n$—CO—$R_{12}$;

i) a group

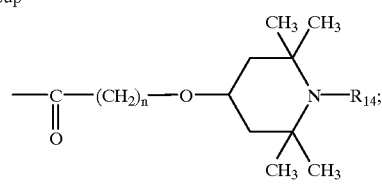

j) a group

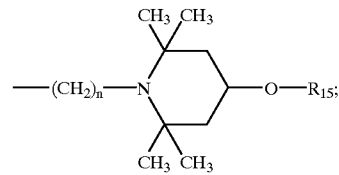

k) a group

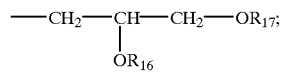

n is 1 to 18;

$R_6$ and $R_7$ are independently of one another H or $C_1$–$C_6$ alkyl;

$R_8$ is $C_1$–$C_{18}$alkyl, $C_2$–$C_8$alkenyl, $C_3$–$C_{20}$ alkyl which is interrupted by one or more O or substituted by OH or is $C_3$–$C_8$alkynyl;

$R_9$ and $R_{10}$ are independently of one another $C_1$–$C_{12}$ alkyl, $C_3$–$C_{12}$ alkoxyalkyl or $C_5$–$C_{12}$cycloalkyl;

$R_{11}$ is $C_1$–$C_{18}$alkyl or $C_2$–$C_{18}$alkenyl;

$R_{12}$ is $C_1$–$C_{18}$ alkyl, $C_2$–$C_{18}$alkenyl, $C_1$–$C_{12}$alkoxy, $C_1$–$C_{12}$ alkylamino or a group $R_{19}$—COOH, $R_{14}$ is $C_1$–$C_{12}$ alkyl, allyl, cyclohexyl, benzyl, acetyl, acryloyl, Cyclohexyloxy or $C_1$–$C_{12}$-alkoxy, $R_{15}$ is H or $C_1$–$C_{18}$ alkyl optionally interrupted by one or more oxygen atoms;

$R_{16}$ is H, —CO—$R_{11}$, —Si($R_{21}$)($R_{22}$)($R_{23}$), or —COO$R_{24}$;

$R_{17}$ is $C_1$–$C_{18}$ alkyl, $C_2$–$C_{18}$ alkenyl, $C_3$–$C_{24}$ alkyl or $C_2$–$C_{14}$hydroxyalkyl, each of which is interrupted by one or more O atoms, $C_5$–$C_{12}$ cycloalkyl which is unsubstituted or substituted by 1–3 $C_1$–$C_8$ alkyl, or —CO$R_{11}$, or is

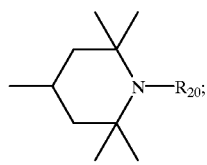

$R_{19}$ is $C_1$–$C_{18}$ alkylene or vinylene;

$R_{20}$ is H, OH, oxyl, $C_1$–$C_{18}$ alkyl, $C_2$–$C_{18}$ alkenyl, $C_1$–$C_{18}$ alkoxy, $C_5$–$C_{12}$ ycloalkyl, $C_5$–$C_{12}$-cycloalkoxy, $C_3$–$C_8$ alkynyl, $C_1$–$C$, alkanoyl, $C_3$–$C_5$alkenoyl or glycidyl;

$R_{21}$, $R_{22}$ and $R_{23}$ are independently of one another $C_1$–$C_6$ alkyl;

$R_{24}$ is $C_1$–$C_4$ alkyl.

3. A composition according to claim 1 wherein in formula I $R_5$, $R_6$ and $R_7$ are H;

$R_1$, $R_2$, $R_3$ and $R_4$ are the same and can be either:

a) $C_1$–$C_{18}$ straight chain or branched alkyl;

b) cyclohexyl;

e) allyl;

f) $C_3$–$C_{18}$ alkyl which is interrupted by one or more a atoms;

g) —CO—$R_{12}$;

i) a group

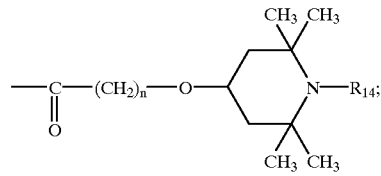

j) a group

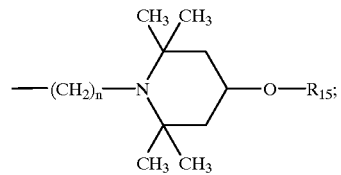

k) a group

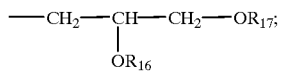

n is 1 to 6;

$R_{12}$ is $C_1$–$C_4$alkyl or $C_2$–$C_3$alkenyl;

$R_{14}$ is $C_1$–$C_{12}$alkyl, benzyl, or $C_5$–$C_8$cycloalkyl; most preferably $C_6$–$C_{10}$alkyl or cyclohexyl.

$R_{15}$ is H or $C_1$–$C_{18}$alkyl optionally interrupted by one or more oxygen atoms $R_{16}$ is H, —CO—R, or —COO$R_{24}$;

$R_{17}$ is $C_1$–$C_{18}$alkyl, $C_2$–$C_{18}$alkenyl, $C_3$–$C_{24}$alkyl or $C_2$–$C_{14}$ hydroxyalkyl, each of which is interrupted by one or more O atoms or is $C_5$–$C_{12}$ cycloalkyl; or is

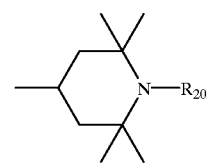

$R_{20}$ is H, $C_1$–$C_8$alkyl, acetyl, propargyl, acryloyl, $C_1$–$C_8$ alkoxy or $C_5$–$C_{12}$cycloalkyl; $R_{24}$ is $C_1$–$C_4$ alkyl.

4. A composition according to claim 1 which contains at least one additional phosphite stabilizer.

5. A composition according to claim 4 wherein the phosphite stabilizer is tris-(2,4-di-tert-butylphenyl)-phosphite.

6. A composition according to claim 1 which contains at least one additional phenolic antioxidant.

7. A composition according to claim 1 wherein the spiroindane compound is present in a quantity of from 0.05 to 10% by weight, based on the weight of the total solids of the powder coating composition.

8. A process for stabilizing a coating material or paint which comprises adding thereto an effective stabilizing amount of a compound of the formula I as described in claim 1.

9. A compound of formula I as described in claim 1, with the proviso that at least one of $R_1$ to $R_4$ is a group i), j) or k) wherein $R_{17}$ is a group

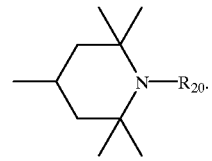

* * * * *